US012539234B2

(12) United States Patent
Kalyanasundaram et al.

(10) Patent No.: US 12,539,234 B2
(45) Date of Patent: Feb. 3, 2026

(54) OCULAR DRUG DELIVERY DEVICES

(71) Applicants: Indian Institute of Technology Delhi, New Delhi (IN); All India Institute Of Medical Sciences, New Delhi (IN)

(72) Inventors: Dinesh Kalyanasundaram, New Delhi (IN); Rohan Chawla, New Delhi (IN); Jayanta Bhattacharyya, New Delhi (IN); Lata Kaushik, New Delhi (IN)

(73) Assignees: Indian Institute of Technology Delhi, New Delhi (IN); All India Institute Of Medical Sciences, New Delhi (IN)

( * ) Notice: Subject to any disclaimer, the term of this patent is extended or adjusted under 35 U.S.C. 154(b) by 357 days.

(21) Appl. No.: 17/755,436

(22) PCT Filed: Sep. 2, 2020

(86) PCT No.: PCT/IN2020/050764
§ 371 (c)(1),
(2) Date: Apr. 28, 2022

(87) PCT Pub. No.: WO2021/079376
PCT Pub. Date: Apr. 29, 2021

(65) Prior Publication Data

US 2023/0390108 A1 Dec. 7, 2023

(30) Foreign Application Priority Data

Oct. 24, 2019 (IN) ............................ 201911043252

(51) Int. Cl.
*A61F 9/00* (2006.01)

(52) U.S. Cl.
CPC ................................. *A61F 9/0017* (2013.01)

(58) Field of Classification Search
CPC ..... A61F 9/0008; A61F 9/0017; A61F 9/0026
See application file for complete search history.

(56) References Cited

U.S. PATENT DOCUMENTS 5,466,233 A * 11/1995 Weiner ................. A61K 9/0051 604/890.1
5,707,643 A 1/1998 Ogura et al.
(Continued)

FOREIGN PATENT DOCUMENTS

ES 2493921 T3 * 9/2014 ........... A61F 9/0017
IN 201811047294 A 2/2019

OTHER PUBLICATIONS

BNW Valve Manufacturing, Zero Leakage Flap Valve, Feb. 25, 2017 (Year: 2017).*
(Continued)

*Primary Examiner* — Rebecca E Eisenberg
*Assistant Examiner* — Matthew Wrubleski
(74) *Attorney, Agent, or Firm* — Workman Nydegger

(57) ABSTRACT

An ocular drug delivery device is disclosed. The ocular drug delivery device includes a top portion having an opening adapted to receive an injection needle to deliver drug into an eye. Further, the ocular drug delivery device includes a bottom portion extending from the top portion. The bottom portion includes a cavity to accommodate a valve. The valve is adapted to be pushed by the injection needle. Further, the ocular drug delivery device includes a securing portion attached to the top portion. The securing portion is adapted to secure the ocular drug delivery to the eye.

6 Claims, 8 Drawing Sheets

(56) References Cited

U.S. PATENT DOCUMENTS

| | | | |
|---|---|---|---|
| 6,251,090 B1 | 6/2001 | Avery et al. | |
| 6,719,750 B2 | 4/2004 | Varner et al. | |
| 2003/0014036 A1* | 1/2003 | Varner .............. | A61M 39/0208 604/521 |
| 2009/0196903 A1* | 8/2009 | Kliman ................... | A61P 27/02 424/423 |
| 2013/0245544 A1* | 9/2013 | de Juan, Jr. ............. | A61M 5/46 604/44 |
| 2019/0117454 A1* | 4/2019 | Campbell ............ | A61K 9/0051 |

OTHER PUBLICATIONS

International Search Report and Written Opinion, mailed Dec. 10, 2020, from PCT/IN2020/050764 filed Sep. 2, 2020.

India Examination Report, mailed May 27, 2021, from India Pat. App. No. 201911043252, 5 pages.

* cited by examiner

OCULAR DRUG DELIVERY DEVICES

FIELD OF THE INVENTION

The present disclosure relates to drug delivery devices and, more particularly, to ocular drug delivery devices.

BACKGROUND

Since the discovery of agents which can be injected into the vitreous to treat various retinal disorders, the procedures involving repeated intravitreal injections have increased tremendously. In fact, the number of intravitreal injections given surpassed the number of cataract surgeries (the top surgical procedure) being done in America in 2010. Currently, an approximately 5.9 million intravitreal injections are performed every year in America covered by Medicare alone.

The sudden surge in the number of these injections occurred when drugs like Ranibizumab and Bevacizumab were introduced for the treatment of Age Related Macular Degeneration (ARMD) and other retinal vascular disorders like Diabetic macular edema, Proliferative diabetic retinopathy and retinal vascular occlusions. Various studies have shown a high efficiency of anti-VEGF monoclonal antibodies in reducing visual loss and enhancing visual acuity in these disorders.

However, a significant challenge in the use of these agents is that the effect of the drug is short term, lasting from 1 to 3 months, depending upon the pathology. To maintain the visual gain achieved by these drugs, the intra-ocular injection has to be repeated at regular intervals. This accounts for the high number of these procedures being performed worldwide.

Although, there are various issues related to re-injection procedure. For instance, the patient has to undergo a painful procedure of injections that pierce the ocular coats. Further, repeated injections are accompanied by an increased risk of intraocular infections such as endophthalmitis. Some studies have found the rate of these infections to be around 0.049% (nearly 0.05%). Furthermore, for each procedure, the patient has to be shifted to the operating room (OR) as a policy in most centres of India and Europe. In America it is performed in a clean injection room and not the OR, probably due to the high costs involved. Also, re-injection may discourage many patients to stop treatment as it is a cumbersome, painful, expensive, and a never-ending therapeutic procedure. Drop off rate in the real world is high.

Devices available in the market to address the above-mentioned problems are quite a few and far. There are implantable devices available having drug reservoirs sustained release over time. These drug reservoirs need to be filled at regular intervals. However, the presence of the drug reservoir may make the device bulky and increase the design complexity leading to an enhanced risk of device failure.

SUMMARY OF THE INVENTION

This summary is provided to introduce a selection of concepts, in a simplified format, that are further described in the detailed description of the invention. This summary is neither intended to identify key or essential inventive concepts of the invention and nor is it intended to determine the scope of the invention.

The current invention presents a novel, minimally invasive drug delivery device relating to intraocular drug delivery. Current methodologies, products and technologies, however effective, are not patient compliant as they need repeated piercing of the ocular tissues and they focus on decreasing the frequency of drug administration. Whereas, the current drug delivery device is devised for repeated and painless drug delivery without having to pierce the biological layers every time. It shall be placed over the surface of the intended part, while the body of the drug delivery device pierces through the layers. The drug delivery device shall be implanted in a minor surgery and shall be used as a short term or long-term implant based on the intended use. Drug delivery device shall also be used for other applications pertaining to surpassing multiple biological layers. The device also aims at providing a sustained release of the drug over a period of time. The device incorporates a gel which results in sustained release of the drug to maintain therapeutic concentration. This also helps to restrict efflux of the intraocular content from an inner portion of the eye.

In an embodiment of the present disclosure, an ocular drug delivery device is disclosed. The ocular drug delivery device of the present invention has a top portion having an opening adapted to receive an injection needle to deliver drug into an eye and a bottom portion extending from the top portion. Further, the bottom portion of the device has a cavity to accommodate a valve, wherein the valve is adapted to be pushed by the injection needle. Further, a securing portion is attached to the top portion, wherein the securing portion is adapted to secure the device to the eye.

In another embodiment of the present disclosure, an ocular drug delivery device is disclosed. The ocular drug delivery device includes a top portion having an opening adapted to receive an injection needle to deliver drug into an eye. Further, the ocular drug delivery device includes a bottom portion distal to the top portion and adapted to be inserted in the eye. The ocular drug delivery device includes a body extending between the top portion and the bottom portion. A cavity is defined in the body and is in fluid communication with the opening. The cavity is adapted to deliver the drug into the eye. A plurality of openings is formed on the body, wherein each of the plurality of openings is adapted to be in fluid communication with the cavity. The drug from the cavity is released through the plurality of openings.

To further clarify the advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1:
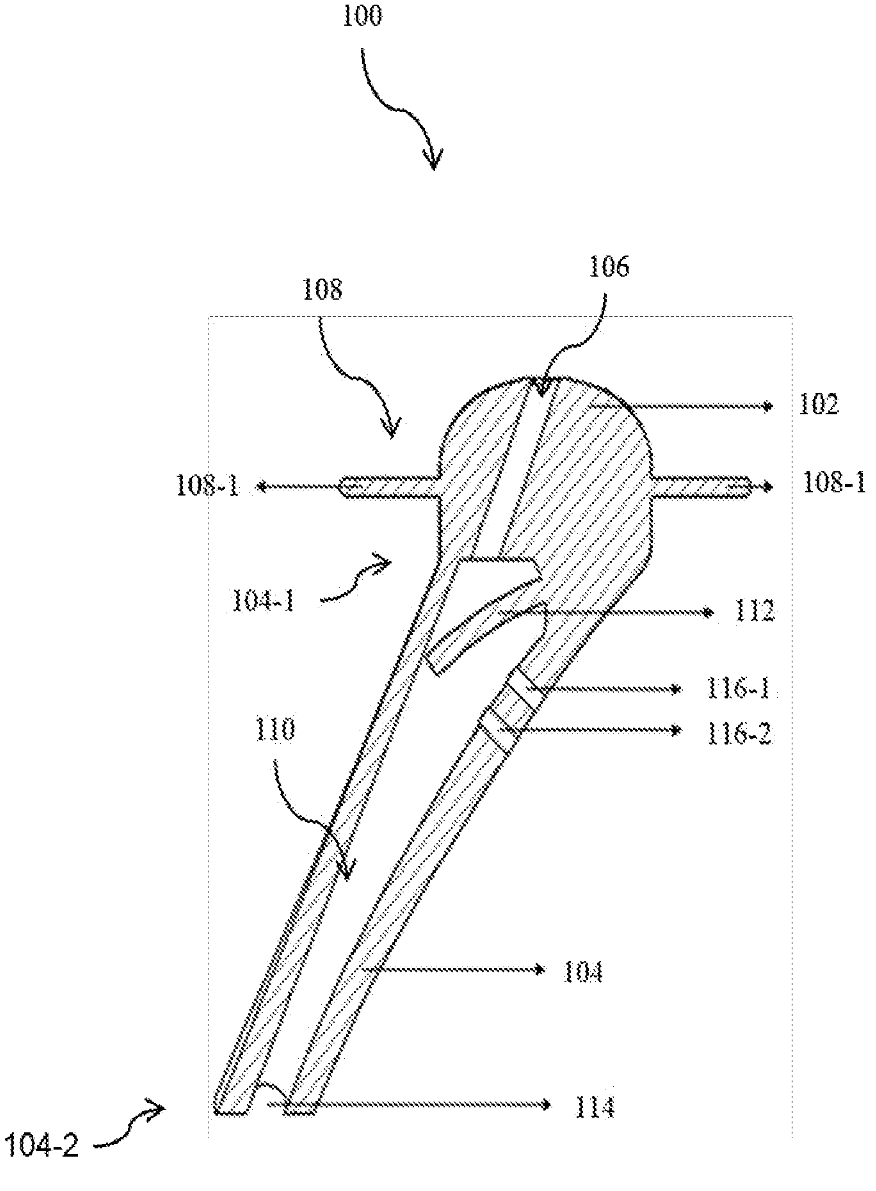
FIG. 1 illustrates a sectional view of an ocular drug delivery device, according to an embodiment of the present disclosure.

Further, skilled artisans will appreciate that elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION OF FIGURES

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

The term "some" as used herein is defined as "none, or one, or more than one, or all." Accordingly, the terms "none," "one," "more than one," "more than one, but not all" or "all" would all fall under the definition of "some." The term "some embodiments" may refer to no embodiments or to one embodiment or to several embodiments or to all embodiments. Accordingly, the term "some embodiments" is defined as meaning "no embodiment, or one embodiment, or more than one embodiment, or all embodiments."

The terminology and structure employed herein is for describing, teaching and illuminating some embodiments and their specific features and elements and does not limit, restrict or reduce the spirit and scope of the claims or their equivalents.

More specifically, any terms used herein such as but not limited to "includes," "comprises," "has," "consists," and grammatical variants thereof do NOT specify an exact limitation or restriction and certainly do NOT exclude the possible addition of one or more features or elements, unless otherwise stated, and furthermore must NOT be taken to exclude the possible removal of one or more of the listed features and elements, unless otherwise stated with the limiting language "MUST comprise" or "NEEDS TO include."

Whether or not a certain feature or element was limited to being used only once, either way, it may still be referred to as "one or more features" or "one or more elements" or "at least one feature" or "at least one element." Furthermore, the use of the terms "one or more" or "at least one" feature or element do NOT preclude there being none of that feature or element, unless otherwise specified by limiting language such as "there NEEDS to be one or more . . . " or "one or more element is REQUIRED."

Unless otherwise defined, all terms, and especially any technical and/or scientific terms, used herein may be taken to have the same meaning as commonly understood by one having ordinary skills in the art.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfil the requirements of uniqueness, utility and non-obviousness.

Use of the phrases and/or terms such as but not limited to "a first embodiment," "a further embodiment," "an alternate embodiment," "one embodiment," "an embodiment," "multiple embodiments," "some embodiments," "other embodiments," "further embodiment", "furthermore embodiment", "additional embodiment" or variants thereof do NOT necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

Embodiments of the present invention will be described below in detail with reference to the accompanying drawings.

FIG. 1 illustrates a sectional view of an ocular drug delivery device 100, according to an embodiment of the present disclosure. The ocular drug delivery device 100 may be adapted to be implanted to deliver drug into an eye. The ocular drug delivery device 100 may be employed to deliver the drug intra-ocularly into the vitreous to treat various retinal disorders. The ocular drug delivery device 100 may substantially eliminate the requirement of repeated intravitreal injections. The ocular drug delivery device 100 may be implanted by a minor surgical procedure and placed on the eye penetrating ocular layers. Further, the ocular drug delivery device 100 may be adapted to allow injection of the drug via an injection needle and syringe directly into the eye.

Figure 2:
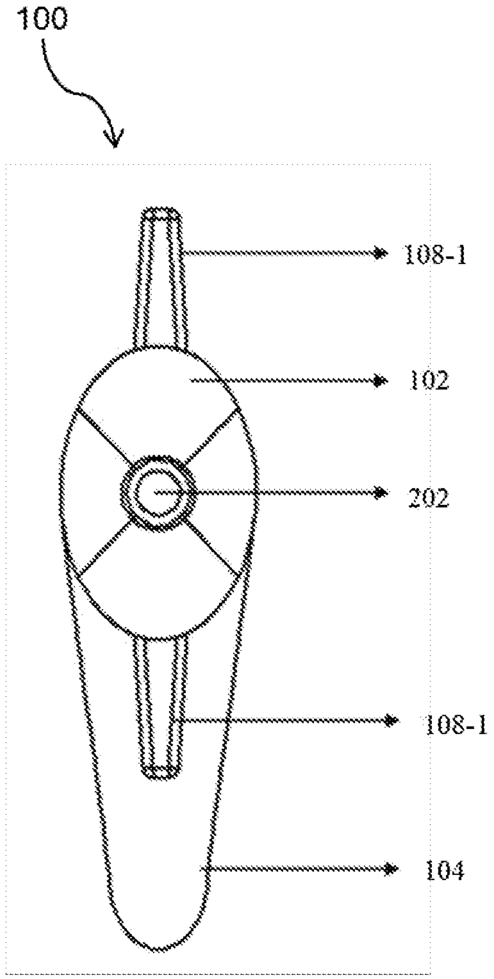
FIG. 2 illustrates a top view of an ocular drug delivery device, according to an embodiment of the present disclosure.
Figure 3:
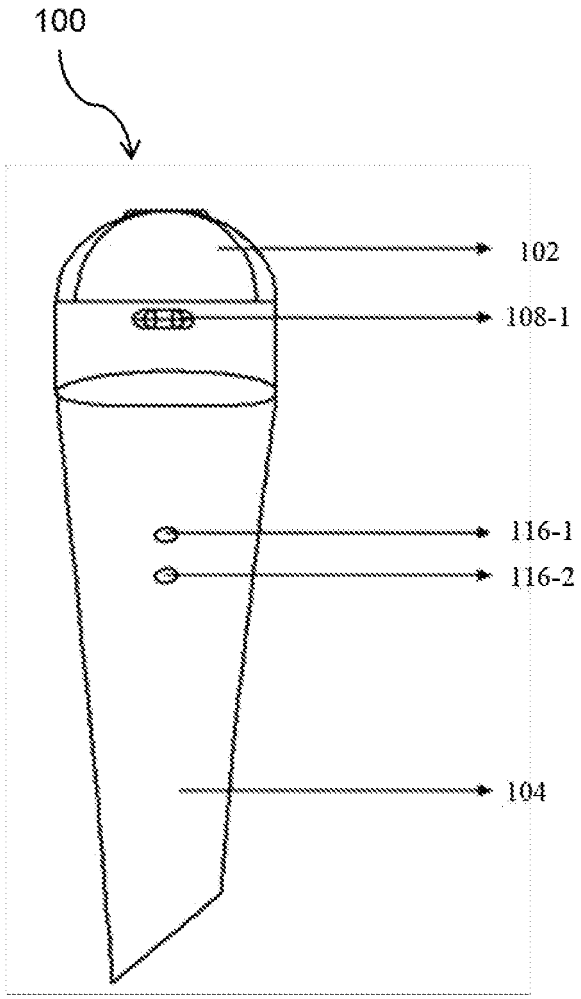
FIG. 3 illustrates a front view of an ocular drug delivery device, according to an embodiment of the present disclosure.
Figure 4:
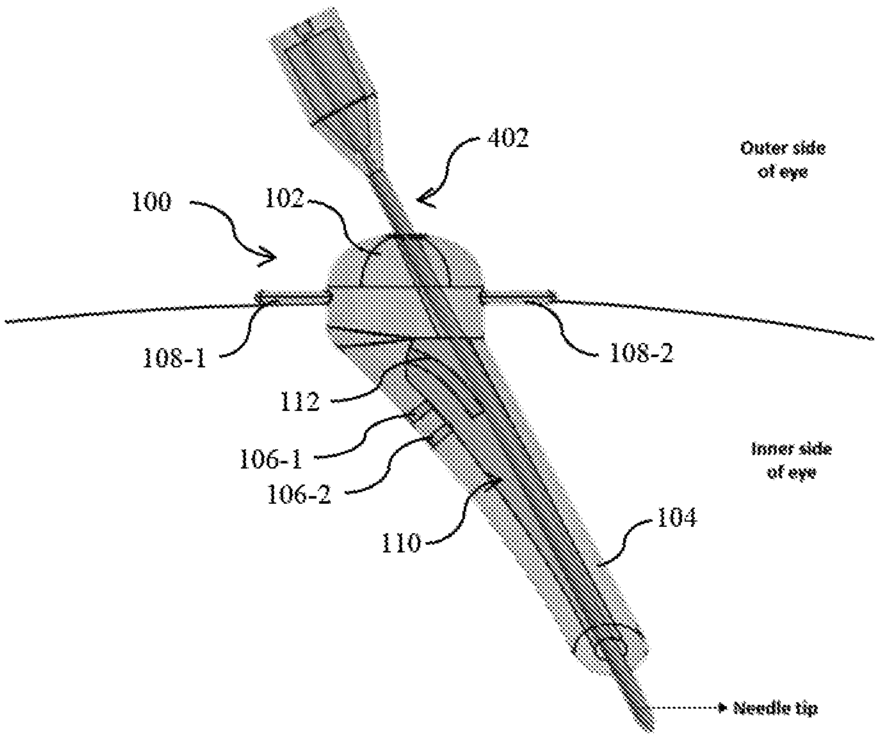
FIG. 4 illustrates a perspective view of the ocular delivery device secured to an eye, according to an embodiment of the present disclosure.

FIG. 2 illustrates a top view of the ocular drug delivery device 100, according to an embodiment of the present disclosure. FIG. 3 illustrates a front view of the ocular drug delivery device 100, according to an embodiment of the present disclosure. FIG. 4 illustrates a perspective view of the ocular delivery device 100 secured to the eye, according to an embodiment of the present disclosure. In an embodiment, the ocular drug delivery device 100 may interchangeably be referred to as the delivery device 100, without departing from the scope of the present disclosure.

Referring to FIGS. 1-4, the delivery device 100 may include a top portion 102 and a bottom portion 104 distal to the top portion 102. The top portion 102 may be adapted to be positioned on a surface under the conjunctiva of the eye. The top portion 102 may include an opening 202 (shown in FIG. 2) adapted to receive an injection needle 402 (shown in FIG. 4) to deliver the drug into the eye.

As shown in FIG. 1, the top portion 102 may include a first channel 106 extending from the opening 202 of the top portion 102. The first channel 106 may be adapted to accommodate at least a portion of the injection needle, when the injection needle is inserted through the opening 202 to deliver the drug into the eye. Further, referring to FIG. 2, the opening 202 may be provided with a septum or a membrane to prevent ingress of contaminants in the first channel 106 through the opening 202. As explained earlier, the top portion 102 may be sutured to a portion of the eye under the conjunctiva such that the conjunctiva protects the delivery device 100 from any outer environment contamination.

In the illustrated embodiment, the top portion 102 may have a substantially oval shape, without departing from the scope of the present disclosure. However, it should be appreciated by a person skilled in the art that it should not be construed as limiting, and the top portion 102 of the delivery device 100 may have any other shape, without departing from the scope of the present disclosure.

Further, the delivery device 100 may include a securing portion 108 attached to the top portion 102. The securing portion 108 may be adapted to secure the delivery device 100 to the eye. In an embodiment, the securing portion 108 may include a pair of flaps 108-1, 108-2 extending outwardly from the top portion 102. The pair of flaps 108-1, 108-2 may be positioned opposite to each other on the top portion 102. Each of the pair of flaps 108-1, 108-2 may be adapted to be sutured to sclera of the eye to secure the delivery device 100 to the eye. Although, in the illustrated embodiment, the securing portion 108 includes the pair of flaps 108-1, 108-2 for securing the delivery device 100 to the eye. It should be appreciated by a person skilled in the art that it should not be construed as limiting, and the securing portion 108 may include any other provision(s) for securing the delivery device 100 to the eye, without departing from the scope of the present disclosure Further, the delivery device 100 may include the bottom portion 104 extending from the top portion 102. In the illustrated embodiment, the bottom portion 104 includes a first end 104-1 and a second end 104-2 distal to the first end 104-1. The first end 104-1 may be attached to the top portion 102 of the delivery device 100. Further, the bottom portion 104 may include a cavity 110 extending along a length of the bottom portion 104. In an embodiment, the cavity 110 may extend from the first end 104-1 to the second end 104-2 of the bottom portion 104.

The cavity 110 may be in communication with the opening 202 of the top portion 102. In particular, the cavity 110 may be in communication with the opening 202 through the first channel 106 formed in the top portion 102 of the delivery device 100. The cavity 110 may be adapted to accommodate a valve 112. In the illustrated embodiment, the valve 112 may be embodied as a one-way valve. Constructional and operational details of the valve 112 are explained in detail in the later sections of the present disclosure.

Further, the second end 104-2 of the bottom portion 104 includes a beveled opening 114 in communication with the cavity 110. The beveled opening 114 may be adapted to receive the injection needle through the cavity 110 to release the drug inside the eye. As explained earlier, the injection needle may be inserted within the delivery device 100 through the opening 202 and may travel through the cavity 110 to the beveled opening 114. In particular, the injection needle may be projected outwardly through the beveled opening 114 to release the drug inside the eye (as shown in FIG. 4).

In an embodiment, the bottom portion 104 may include a plurality of holes 116-1, 116-2 in communication with the cavity 110 of the bottom portion 104. Each of the plurality of holes 116-1, 116-2 may be formed in the vicinity of the valve 112 disposed within the cavity 110. The plurality of holes 116-1, 116-2 may be adapted to allow a flow of residual fluid from the cavity 110 of the bottom portion 104. In the illustrated embodiment, referring to FIGS. 1-4, the plurality of holes 116-1, 116-2 may include a pair of holes to allow the flow of residual fluid from the cavity 110. However, it should be appreciated by a person skilled in the art that it should not be construed as limiting, and the bottom portion may include multiple holes to allow the flow of residual fluid from the cavity 110.

In the illustrated embodiment, referring to FIG. 1, the bottom portion 104 may substantially have a conical shape, without departing from the scope of the present disclosure. In such an embodiment, the cavity 110 may also have substantially a conical shape. However, it should be appreciated by a person skilled in the art that it should not be construed as limiting, and each of the bottom portion 104 and the cavity 110 of the delivery device 100 may have any other shape, without departing from the scope of the present disclosure.

Further, as explained earlier, the valve 112 may be provided within the cavity 110 of the bottom portion 104. As shown in FIG. 1 and FIG. 4, the valve 112 may be positioned in a vicinity of the first end 104-1 of the bottom portion 104. The valve 112 may be adapted to be pushed by the injection needle. In particular, the value 112 may be pushed by the injection needle in a downward direction within the cavity 110. Owing to such an arrangement, the valve 112 may prevent ingress of any contaminants within the cavity 110 of the delivery device 100, and thereby protecting the eye from contamination.

Figure 6:
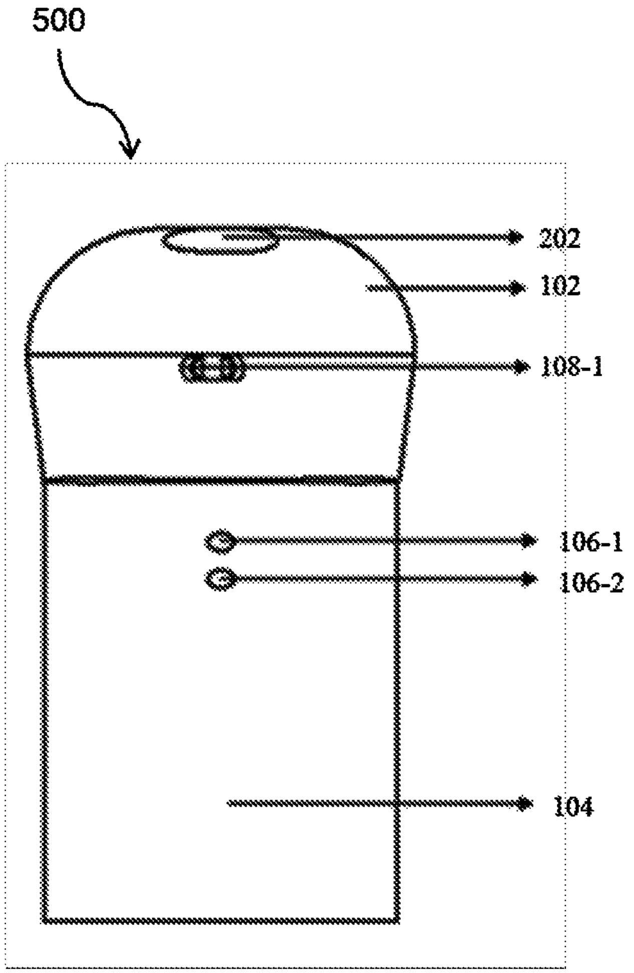
FIG. 6 illustrates a front view of an ocular drug delivery device, according to another embodiment of the present disclosure.
Figure 7A:
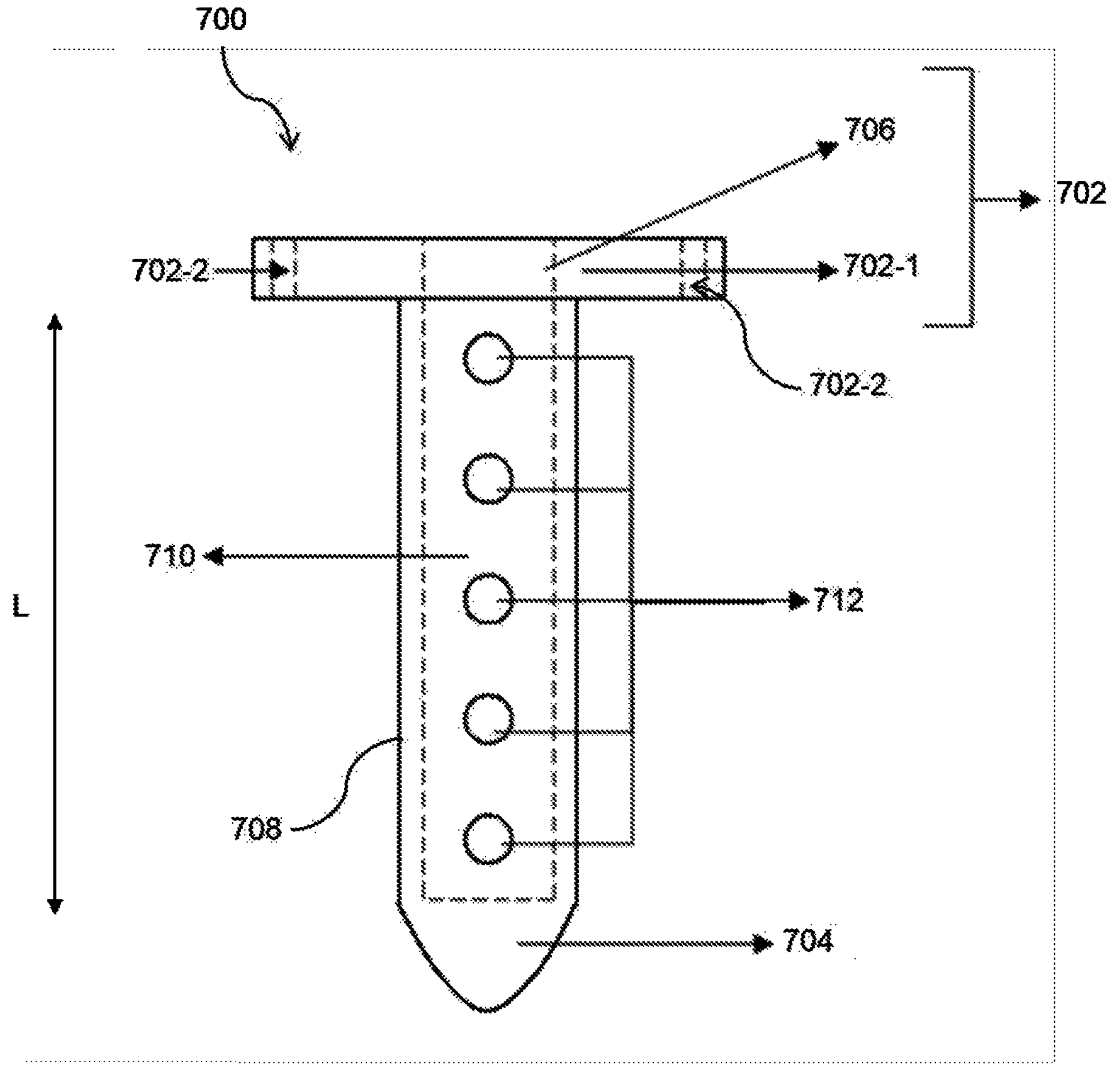
FIG. 7*a* illustrates a front view of an ocular drug delivery device, according to yet another embodiment of the present disclosure.
Figure 7B:
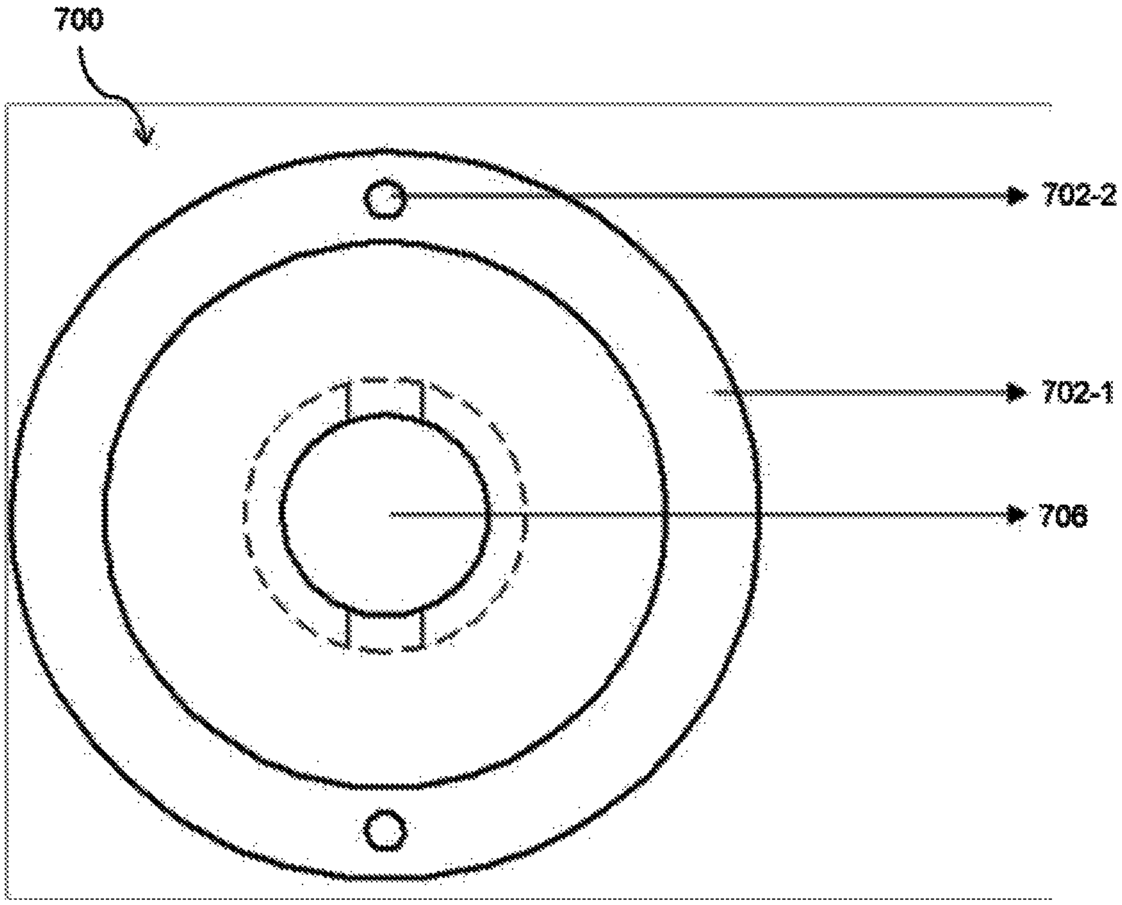
FIG. 7*b* illustrates a top view of the ocular drug delivery device, according to an embodiment of the present disclosure.

As mentioned earlier, the valve 112 may be embodied as a one-way valve adapted to be pushed in a downward direction within the cavity 110. Therefore, the valve 112 restricts fluid efflux from an inner portion of the eye through the cavity 110. The valve may only allow the insertion of the injection needle through the cavity to release liquid or the drug from inside the eye. In an embodiment, the valve 112 may be adapted to restrict efflux of intraocular content from an inner portion of the eye. Referring to FIG. 6, the valve 112 may be adapted to be pushed by the injection needle, when the injection needle is inserted within the cavity 110 through the opening 202 provided at the top portion 102 of the delivery device 100. In particular, when the injection needle is inserted within the cavity 110, the valve 112 may be pushed in a downward direction by the injection needle to allow further movement of the injection needle within the cavity 110 to the beveled opening 114. Subsequently, the injection needle may release the drug through the beveled opening 114 inside an eye.

Further, as explained earlier, the plurality of holes 116-1, 116-2 may be provided at the bottom portion 104 to allow the flow of residual fluid from the cavity 110 of the bottom portion 104. In particular, the valve 112 may be adapted to be pushed by the injection needle such that the valve 112 thrusts the flow of residual fluid from the cavity 110 of the bottom portion 104 through the plurality of holes 116-1, 116-2.

Figure 5:
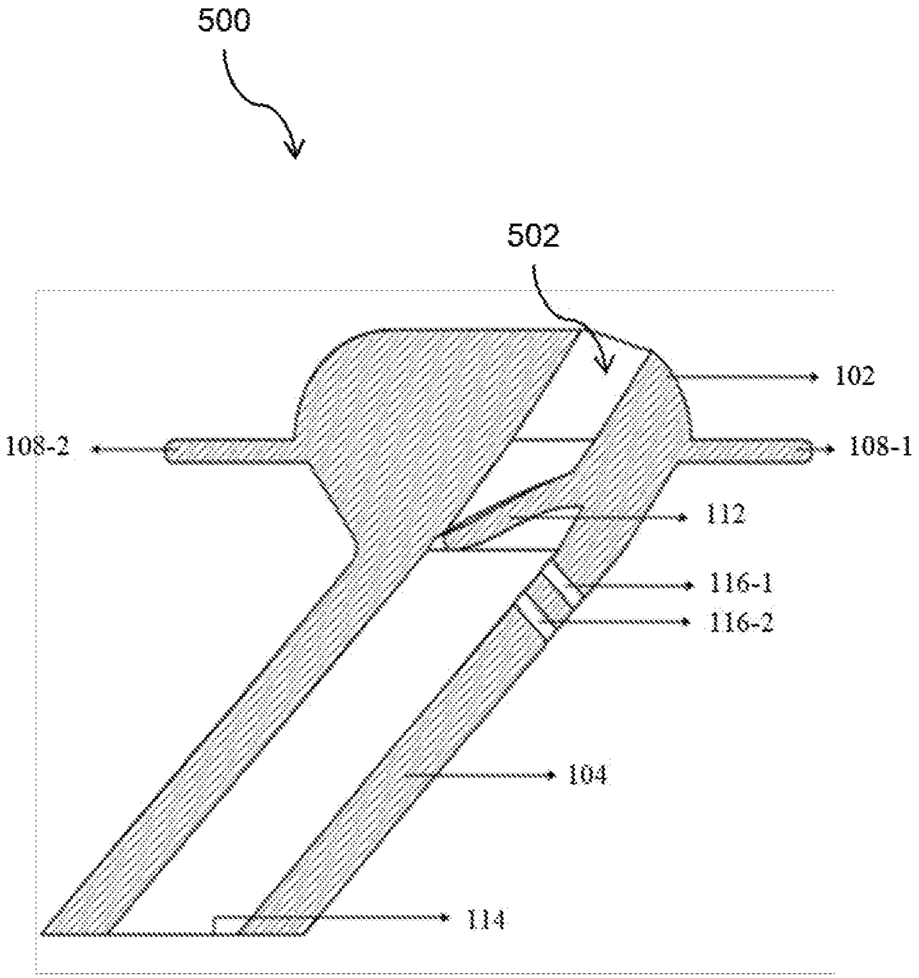
FIG. 5 illustrates a sectional view of an ocular drug delivery device, according to another embodiment of the present disclosure.

FIG. 5 illustrates a sectional view of an ocular drug delivery device 500, according to another embodiment of the present disclosure. FIG. 6 illustrates a front view of the ocular drug delivery device 500, according to another embodiment of the present disclosure. In the illustrated embodiment, the ocular delivery device 500 may interchangeably be referred to as the delivery device 500. For the sake of brevity, details of the present disclosure that are explained in detail in the description of FIG. 1, FIG. 2, FIG. 3, and FIG. 4 are not explained in detail in the description of FIG. 5 and FIG. 6.

Similar to the delivery device 100 explained with respect to FIG. 1, FIG. 2, FIG. 3, and FIG. 4, the delivery device 500 of the illustrated embodiment includes the top portion 102 having the opening 202 adapted to receive the injection needle to deliver drug into the eye. Further, the delivery device 500 includes the bottom portion 104 and the securing portion 108 adapted to secure the ocular drug delivery device to the eye.

However, in the illustrated embodiment, the delivery device includes a cavity 502 extending from the opening 202 of the top portion to the beveled opening 114 of the bottom portion 104. The cavity 502 may be adapted to accommodate the valve 112 to restrict efflux of intraocular content from the inner portion of the eye. Further, in the illustrated embodiment, the cavity 502 may substantially have a cylindrical shape, without departing from the scope of the present disclosure.

FIG. *7a* illustrates a front view of an ocular drug delivery device 700, according to yet another embodiment of the present disclosure. FIG. *7b* illustrates a top view of the ocular drug delivery device 700, according to an embodiment of the present disclosure. In the illustrated embodiment, the ocular drug delivery device 700 may interchangeably be referred to as the delivery device 700.

Referring to FIG. *7a* and FIG. *7b*, the device 700 includes a top portion 702 and a bottom portion 704 distal to the top portion 702. The top portion 702 may have an opening 706 adapted to receive the injection needle to deliver the drug into the eye. The top portion 702 may include a flange 702-1 adapted to be coupled to a surface under the conjunctiva of the eye. In particular, the ocular drug delivery device 700 may be supported on the eye through the flange 702-1 formed at the top portion 702. The flange 702-1 may be adapted to be coupled to the surface using sutures through a plurality of holes 702-2 formed on the flange 702-1.

The bottom portion 704 may be adapted to be inserted in the eye to deliver the drug into the eye. In the illustrated embodiment, the bottom portion 704 has a tapered shape, without departing from the scope of the present disclosure. The tapered shape of the bottom portion 704 may aid in easy insertion of the ocular drug delivery device 700 inside the tissue of the eye. Further, the device 700 includes a body 708 extending between the top portion 702 and the bottom portion 704. The bottom portion 704 along with the body 708 may be inserted in the tissue of the eye in a manner that the top portion 702 abuts the surface under the conjunctiva of the eye. The body 708 may be formed of at least one of materials including, but not limited to, titanium alloys, cobalt chromium alloys, and stainless steels. However, it should be appreciated by a person skilled in the art that it should not be construed as limiting, and the body 708 may be formed of other materials, without departing from the scope of the present disclosure.

The device 700 may include a cavity 710 defined in the body 708 and is in fluid communication with the opening 706. The cavity 710 may be adapted to deliver the drug into the eye. Further, the device 700 may include a plurality of openings 712 formed on the body 708. Each of the plurality of openings 712 may be adapted to be in fluid communication with the cavity 710. The drug from the cavity 710 may be released into the eye through the plurality of opening 712.

In an embodiment, the ocular drug delivery device 700 may be provided to deliver the drug over time in order to maintain therapeutic concentration. The device 700 may incorporate a gel which results in the sustained release of the drug to maintain therapeutic concentration. Further, this also helps to restrict efflux of the injected drug and the intraocular content. In such an embodiment, the cavity 710 may be adapted to be filed with a porous material to absorb the drug and to release the absorbed drug over time. The porous material may be adapted to absorb the drug released by the injection needle in the cavity 710. Subsequently, the porous material may be adapted to release the absorbed drug for delivery into the eye over time. Further, the drug released from the porous material may egress from the body 708 through the plurality of openings 712.

In an embodiment, the porous material may be embodied as at least one of materials including, but not limited to, polymers, ceramics, and metals. The polymers that can be used as the porous material may include, but is not limited to, alginate, silk, collagen, gelatin, agarose, polycaprolactone (PCL), polyethylene glycol (PEG), polyethylene oxide (PEO), poly (lactide-co-glycolic acid (PLGA), polyurethane (PU), polymethacrylates, acrylamides, etc. However, it should be appreciated by a person skilled in the art that it should not be construed as limiting, and the porous material may be embodied as other materials, without departing from the scope of the present disclosure.

In an embodiment, the opening 706 may be covered with a self-sealing material adapted to receive the injection needle. In such an embodiment, the injection needle may be inserted in the cavity 710 through the seal-sealing material. The self-sealing material may be adapted to seal the opening 706 after retraction of the injection needle from the self-sealing material. In particular, the self-sealing material may be adapted to retain shape after retraction of the injection needle through the self-sealing material and thereby, repairing a hole created by the injection needle in the self-sealing material. This substantially decreases the efflux during insertion of the injection needle and after retraction of the injection needle. In an embodiment, the self-sealing material may include, but is not limited to, polymers, such as polydimethylsiloxane (PDMS), polyethylene glycol (PEG), silicones, etc. However, it should be appreciated by a person skilled in the art that it should not be construed as limiting, and the self-sealing material may be embodied as different materials, without departing from the scope of the present disclosure.

The delivery devices 100, 500, 700 of the present disclosure drastically reduce pain associated with the procedure of delivering the drug inside the eye. As the patient is more cooperative for regular drug injection inside the eye due to the drug delivery device of the present invention, it drastically increases compliance towards the newer monoclonal antibody-based retinal therapies which need unending, life-long injections at regular intervals. The delivery devices 100, 500, 700 may also be employed to inject intraocular antibiotics in cases of Endophthalmitis at more frequent intervals with ease. Further, the delivery devices 100, 500, 700 may be employed to deliver chemotherapeutic agents such as methotrexate in cases of intraocular lymphoma. In such patients also, biweekly injections are required initially and then maintenance dose continues for months. Therefore, the delivery devices 100, 500, 700 have a wide range of applications.

Further, the delivery devices 100, 500, 700 may be advantageous for the patient requiring an intermittent drug injection into the eye. Some drugs that are required to be injected at regular interval e.g. ranibizumab preventing blindness in over 90% of test subjects in clinical trials can be injected through the delivery devices 100, 500, 700 with ease. Further, the delivery devices 100, 500 of the present disclosure substantially eliminates requirement of a drug reservoir for supplying the drug. This allows the delivery devices 100, 500, 700 to be implemented with ease for injecting drugs which cannot be stored for longer period of time for sustained release. Therefore, the delivery devices 100, 500, 700 can be implemented for injecting drugs as per requirement, such as dosage requirement. Further, overall weight of the delivery devices 100, 500, 700 is substantially reduced. Furthermore, the delivery devices 100, 500, 700 may substantially reduce pain and discomfort involved during piercing of the eye.

The delivery devices 100, 500, 700 of the present disclosure consists of a cavity 710 with multiple exit holes, i.e., the plurality of holes 712. The cavity 710 can be covered with the self-sealing membrane on the top in order to minimize efflux. This may also limit the contact of the biological fluids with the external environment. As explained earlier, in another embodiment, the cavity can be filled with the porous material which can absorb the drug and subsequently release the drug into the eye over time. This gives an advantage of stabilizing the antibodies or antibody fragments in the anti-VEGF drugs such as Avastin and Lucentis. As the pharmaceutical agent may be active for a longer time, it can in turn reduce the frequency of the injections. In an implementation, the delivery devices 100, 500, 700 do not need any specialized mechanism for injection, a regular 30 G or 32 G needle can be used to inject the drug into the delivery devices 100, 500, 700 when required. This makes it widely applicable in developing nations, where any type of extra cost decreases the number of patients that can afford it. The delivery devices 100, 500, 700 is made up of biocompatible metallic material which does not allow piercing of the needle through the its walls. Further, the delivery devices 100, 500, 700 are not complex in design and therefore, can be easily manufactured without substantial increase in the cost. Therefore, the delivery devices 100, 500 of the present disclosure is flexible in implementation, compact, cost-effective, convenient, and has a wide range of applications.

We claim:

1. An ocular drug delivery device, comprising:

a top portion having an opening adapted to receive an injection needle to deliver drug into an eye;

a bottom portion extending from the top portion, the bottom portion having an opening adapted to receive the injection needle, wherein the bottom portion comprises a plurality of holes;

a cavity extending from the opening of the top portion to the opening of the bottom portion, wherein the cavity accommodates a valve adapted to be pushed by the injection needle, wherein each of the plurality of holes is positioned on a same side of the valve in the bottom portion, wherein the plurality of holes is positioned such that opening the valve thrusts residual fluid from the cavity through the plurality of holes into the eye, wherein the valve covers the plurality of holes when in an open position; and a securing portion attached to the top portion, wherein the securing portion is adapted to secure the device to the eye, wherein the securing portion comprises a pair of flaps extending outwardly from the top portion, and wherein the pair of flaps are positioned opposite to each other on the top portion, wherein the cavity is configured to receive the injection needle at an angle.

2. The device of claim 1, wherein the cavity has a cylindrical shape.

3. The device of claim 1, wherein the top portion is adapted to be positioned on a surface under the conjunctiva of the eye.

4. The device of claim 1, wherein each of the pair of flaps is adapted to be sutured to sclera of the eye to secure the device to the eye.

5. The device of claim 1, wherein the opening of the bottom portion is a beveled opening, wherein the beveled opening is in communication with the cavity and is adapted to receive the injection needle through the cavity to release the drug inside the eye.

6. The device of claim 1, wherein the valve includes a one-way valve adapted to restrict efflux of intraocular content from an inner portion of the eye.

* * * * *